United States Patent [19]

Vodian et al.

[11] Patent Number: 4,853,325

[45] Date of Patent: Aug. 1, 1989

[54] SALIVA TEST FOR FELINE LEUKEMIA VIRUS

[75] Inventors: Morton A. Vodian, Escondido; Eric S. Bean, San Diego; Eric D. LeMoine, Poway, all of Calif.

[73] Assignee: Synbiotics Corporation, San Diego, Calif.

[21] Appl. No.: 844,098

[22] Filed: Mar. 26, 1986

[51] Int. Cl.$^4$ ............... G01N 33/569; G01N 33/577
[52] U.S. Cl. ........................... 435/5; 435/7; 435/805; 435/810; 422/58; 436/543; 436/810; 436/813; 530/826
[58] Field of Search .............. 424/88, 89; 435/5, 7, 435/805, 810; 436/810, 543, 813; 422/58; 530/826

[56] References Cited

U.S. PATENT DOCUMENTS

| | | | |
|---|---|---|---|
| 3,826,619 | 7/1974 | Bratu, Jr. et al. | 436/810 |
| 4,017,597 | 4/1977 | Reynolds | 436/810 |
| 4,066,646 | 1/1978 | LeBlanc, Jr. et al. | 436/810 |
| 4,116,638 | 9/1978 | Kenoff | 436/810 |
| 4,126,671 | 11/1978 | House et al. | 424/12 |
| 4,135,884 | 1/1979 | Shen | 422/59 |
| 4,305,924 | 12/1981 | Piasio et al. | 424/1 |
| 4,379,839 | 4/1983 | Spiegelman | 435/5 |
| 4,444,880 | 4/1984 | Tom | 435/7 |
| 4,533,629 | 8/1985 | Litman et al. | 435/7 |
| 4,540,660 | 9/1985 | Harte et al. | 435/7 |
| 4,663,277 | 5/1987 | Wang | 435/5 |
| 4,663,436 | 5/1987 | Elder et al. | 530/324 |

OTHER PUBLICATIONS

*Alternative Immunoassays*, W. P. Collins, ed, John Wiley & Sons, Chichester, 1985, p. 235.
Hiramatsu, "Direct Assay of Cortisol in Human Saliva by Solid Phase Radioimmunoassay and Its Clinical Applications", Clin. Chim. Acta, 117 (1981), 239-249.
Preti et al, "ELISA for Salivary and Plasma Estriolin Pregnancy", Steroids, 43(5), May 1984, pp. 469-479.
Walker et al, "Adrenal Status Assessed by Direct Radioimmunoassay of Cortisol in Whole or Parotid Saliva", Clin. Chem., 24(9), 1460-63 (1978).
Lutz et al., Am. J. Vet. Res. (1983), 44:2054-2059.
Saxinger, Intervirology (1981), 15:1-9.
Mia et al., Comp. Immun. Microbiol. Infect. Dis. (1981), 4:111-117.
Francis et al., Leukemia Research (1979), 3:435-441.
Francis et al., J. Clin. Pathol. (1979), 32:514-515.
Francis et al., J. Clin. Microbiol. (1979) 9:154-156.
Francis et al., Nature (1977), 269:252-254.
Hoover et al., Cancer Research (1977), 37:3707-3710.

*Primary Examiner*—Christine M. Nucker
*Attorney, Agent, or Firm*—Martin A. Voet

[57] ABSTRACT

The saliva test for feline leukemia virus (FeLV) employs a probe having an immunochemically sensitive member for collecting saliva from the oral cavity of a cat and employs ELISA reagents for the incubation of the probe and the development of color reactions to indicate the presence or absence of FeLV within the saliva sample collected onto the probe.

19 Claims, 1 Drawing Sheet

SALIVA TEST FOR FELINE LEUKEMIA VIRUS

BACKGROUND OF THE INVENTION

The invention relates to analytical methods and devices for the detection of feline leukemia virus (FeLV) and antigens thereof in the saliva of cats. More particularly, the invention relates to methods and devices for acquiring saliva samples and to immunoassay procedures and kits for detecting the presence of FeLV and FeLV antigens in saliva samples.

The spread of feline leukemia caused by FeLV poses a significant health problem in many cat populations. There is evidence that horizontal transmission of FeLV within cat populations contributes significantly to the occurance of feline leukemia. Transmission of FeLV may cause transient or persistant viremia, which may then lead to leukemia and/or various other fatal pathologies. Evidence suggests that the saliva of viremic cats can carry infectious virus and that cat saliva may serve as an agent for the horizontal transmission of FeLV.

The detection of FeLV viremia is useful for identifying cats which may develop leukemia or other pathologies associated with FeLV. Cats having a FeLV viremia may have a diminished economic value. Additionally, some cat owners may wish to isolate infected cats for observation and to eliminate cats which are persistant excretors of FeLV and FeLV antigens. Eliminations of the persistant excretors diminishes the risk or horizontal transmission of FeLV into population clusters.

Several serum assays have been developed for the detection of FeLV and FeLV antigens in serum. The LEUKASSAY (TM) is a micro ELISA test based on the principle of the double antibody sandwich technique. The LEUKASSAY (TM) is marketed by Pitman-Moore, Inc., Washington Crossing, New Jersey, U.S.A. and is described by A. S. Mia, D. E. Kahn, M. M. Tierney and J. E. Post (Comparative Immunology, Microbiology and Infectious Diseases, vol. 4(1), pp. 111-117 (1981). The test procedure consists of a first incubation of 50 microliters of serum sample in the polyclonal anti-FeLV antibody-coated well of a micro ELISA plate; a second incubation of polyclonal anti-FeLV antibody peroxidase conjugate within the well; and finally, washing unbound conjugate from the well and incubating with chromogenic substrate so as to indicate the presence of bound conjugate within the well. A substantially identical serum assay is described by Carl Saxinger (Intervirology, vol. 15, pp. 1-9 (1981)).

An improved serum assay is described by Hans Lutz, Neils C. Pedersen, and Gordon H. Theilen (American Journal of Veterinary Research, vol. 44(11), pp. 2054-2059 (1983)). The improved serum assay may be used, in conjunction with other tests, for the detection of immune carriers of FeLV. The improved serum assay employs monoclonal antibody having a specificity for FeLV antigen p27, a nucleocapsid protein antigen of FeLV. The p27 monoclonal antibody is incorporated into a micro ELISA for the analysis of FeLV and FeLV antigens in serum. When used in conjunction with other tests, the monoclonal micro ELISA is helpful in the identification of immune carriers of FeLV.

A number of studies have investigated the presence and properties of FeLV in saliva. The stability and infectivity of FeLV in cat saliva dried onto glass surfaces was described by Donald P. Francis, M. Essex, and Dawn Gayzagian (Journal of Clinical Microbiology, vol. 9(1), pp. 154-156 (1979)). In this study, drooled saliva was collected into an iced petri dish from a FeLV excretor cat narcotized with ketamine hydrochloride and induced to salivate by the application of a drop of atropine onto the tongue. The infectivity of FeLV was compared for freshly drooled saliva and for saliva smeared and dried on a glass surface.

Other studies have employed more direct techniques for the collection of saliva excretions. A collection method employing Dacron (TM) swabs was described by Edward A. Hoover, Richard G. Olsen, Lawrence E. Mathes, and Joseph P. Schaller (Cancer Research, vol. 37, pp. 3707-3719 (1977)). This collection method employed Dacron (TM) swabs to obtain material from the oropharynx. After swapping the oropharynx, the collected material is then expressed from the Dacron (TM) swabs using 1 ml. of Hanks balanced salt solution.

A substantially identical technique was described by D. P. Francis et al. (Journal of Clinical Pathology, vol. 32(5), pp. 4514-4515 (1979); Leukemia Research, vol. 3(6), pp. 435-441 (1979); and Nature, vol. 269, pp. 252-254 (1977)). Francis et al. describe the use of calcium alginate swabs (purchased from Calgiswabs, Inolex, Glenwood, Illinois, U.S.A., but no longer available at that source). Francis et al. demonstrate that there is a quantitative correlation between the FeLV and FeLV antigens found in saliva collected by means of rotating a calcium alginate swab within the cat's buccal crease and the FeLV and FeLV antigens found in saliva collected by drooling into an iced petri dish and pipetted therefrom. After rotation in the buccal crease, the calcium alginate swab should be frozen until the FeLV and FeLV antigens are measured. The calcium alginate swabs are cut and placed in sterile vials containing 1.8 ml McCoy's 5A medium with 15% fetal bovine serum, 100 IU/ml penicillin, 100 micrograms/ml streptomycin, and 0.25 micrograms/ml amphotericin. The vials are then frozen at $-90°$ C., until tested. When thawed, the vials are mechanically agitated and the supernatant is diluted and overlaid onto indicator cells. The calcium alginate swabs have been shown to absorb a constant volume of saliva and allow quantification of the presence of FeLV and FeLV antigens.

Saliva analytes, including FeLV and FeLV antigens, can also be assayed using immunochemically reactive dip sticks. U.S. Pat. No. 4,444,880 (Henry Tom, Apr. 24, 1984) discloses a dip stick having a bibulous support for analyzing saliva samples. The Tom device includes a bibulous support which is impregnated with a composition that prevents interference with the immunoassay. Further dip sticks are disclosed in U.S. Pat. No. 4,135,884 (James Shen, Jan. 23, 1979) and in U.S. Pat. No. 4,305,924 (Piasio et al., Dec. 15, 1981). Both the Shen and Piasio devices could also be employed for assaying saliva analytes, including FeLV and FeLV antigens. However, in both cases, the saliva sample must first be collected and then added to the assay vessel. Neither the Shen nor the Piasio dip stick device can be employed to collect the saliva sample directly from the donor oral cavity.

What is needed is a simple method which employs an immunochemically reactive dip stick to collect a saliva sample directly from the donor's oral cavity and then to assay or test for the presence of FeLV, FeLV antigens, and other saliva borne antigens and analytes directly on the same dip stick by the development of a color reaction.

SUMMARY OF THE INVENTION

The FeLV saliva test is a method for detecting FeLV and FeLV antigens in cat saliva as a tool for diagnosing viremia. The FeLV saliva test employs a probe for acquiring a saliva sample from the cat's mouth and employs the same probe for assaying the saliva sample for the presence of FeLV and FeLV antigens. FeLV and FeLV antigens are detected by means of a sandwich immunoassay.

Because of the relative ease with which saliva samples are acquired, the FeLV saliva test may be preferred by many veterinary clinicians over commonly used FeLV serum assays. The relative safety of the FeLV saliva test is particularly important to the clinician when examining viremic cats because FeLV has been classified as an agent of 'moderate risk' by the U.S. National Cancer Institute, presumably because it can grow in human cells and/or demonstrate oncogenicity in experimental conditions in certain non-feline species.

The FeLV saliva test employs a probe as shown in FIG.'s 1, 2, and 3. The probe is used for both acquiring and assaying the saliva sample. The probe has a handle and an attached immunochemically sensitive member. The immunochemically sensitive member may include two submembers, viz. the test submember and the control submember. The test submember is shown in FIG.'s 4 and 5 to have a ball shape. Coated onto the test submember is immobilized anti-FeLV antibody, which forms the solid phase of the sandwich immunoassay. The immunochemically sensitive member may have a frosted or etched surface texture for increasing its surface area and wettability. When acquiring the saliva sample, the immunochemically sensitive member is inserted into the cat's mouth, preferably in the buccal crease, i.e. the posterior cavity between the jaw and the buccal surface. The probe is then rotated so that saliva becomes wetted onto the immunochemically sensitive member.

The wetted member is then transferred to an incubation vessel containing an incubation solution. The immunochemically sensitive member may include a small nipple which supports the probe within the incubation vessel. The shapes of the immunochemically sensitive member and the bottom interior of the incubation vessel are coordinated and complimentary, so that, when supported by the nipple within the incubation wheel, the immunochemically sensitive member is submerged by a small volume of the incubation solution. Use of this small volume reduces the incubation time by shortening the diffusion distances required for formation of the sandwich complex.

After this point, standard sandwich immunoassay protocols may be employed. The incubation solution has a composition which includes a soluble enzyme conjugate of the anti-FeLV antibody. During the incubation process, the antibody-antigen-antibody sandwich forms, consisting of the enzyme conjugate, the FeLV or FeLV antigen, and the immobilized anti-FeLV attached to the test submember. In this manner, the soluble enzyme conjugate of anti-FeLV antibody becomes immobilized onto the immunochemically sensitive member. After the incubation, the unbound components are rinsed off, leaving the sandwich configuration bound to the solid phase. The amount of enzyme conjugate which remains bound to the solid phase is, to a first approximation, proportional to the presence of FeLV and FeLV antigens in the saliva sample.

After rinsing off the unbound components, the presence of enzyme conjugate on the solid phase may then be detected by developing the probe with chromogenic substrates. Either precipitating substrates or non-precipitating substrates may be employed. Precipitating substrates cause color to be deposited onto the probe itself. Non-precipitating substrates cause the development solution to change color.

If a precipitating substrate is employed, the immunochemically sensitive member may include a control submember. Positive color formation on the control submember indicates that both the incubating solution and the chromogenic substrates are active. In a preferred embodiment, the control submember is formed by coating anti-immunoglobulin antibody onto the nipple. The anti-immunoglobulin antibody binds to the anti-FeLV antibody component of the soluble enzyme conjugate. The control portion should always show a positive color reaction when incubated with the incubating solution and developed with the chromogenic substrate.

If a non-precipitating substrate is employed, the clinician may wish to use a test probe and a separate control probe. The control probe will cause solution of chromogenic substrate to change color if the conjugated enzyme has retained its activity.

In an alternative method, the FeLV saliva test may be employed to detect the presence of FeLV specific IgA in saliva. For the FeLV specific IgA test, either FeLV antigenic material or anti-idiotypic antibody raised from FeLV may be employed for the solid phase and the soluble enzyme conjugate. Otherwise, the protocols are analogous to the above FeLV saliva test.

Analogous tests can also be employed for detecting other saliva borne viruses, including other leukemia/leukosis/lymphoma viruses. Examples of such further viruses include feline sarcoma virus (FeSV), human T cell leukemia/lymphoma virus-3 and possibly human T cell leukemia/lymphoma virus-1, bovine leukemia virus (BLV), and avian leukosis virus (ALV). In each case, antibodies having the appropriate specificities are substituted for the solid phase immobilized anti-FeLV antibodies and the soluble enzyme conjugated anti-FeLV antibodies described above.

The FeLV saliva test is novel because it is the first such test which employs the identical instrument for acquiring the saliva sample and for performing the immunoassay.

DETAILED DESCRIPTION

Figures 1, 2, 3, 4, 5, 6:
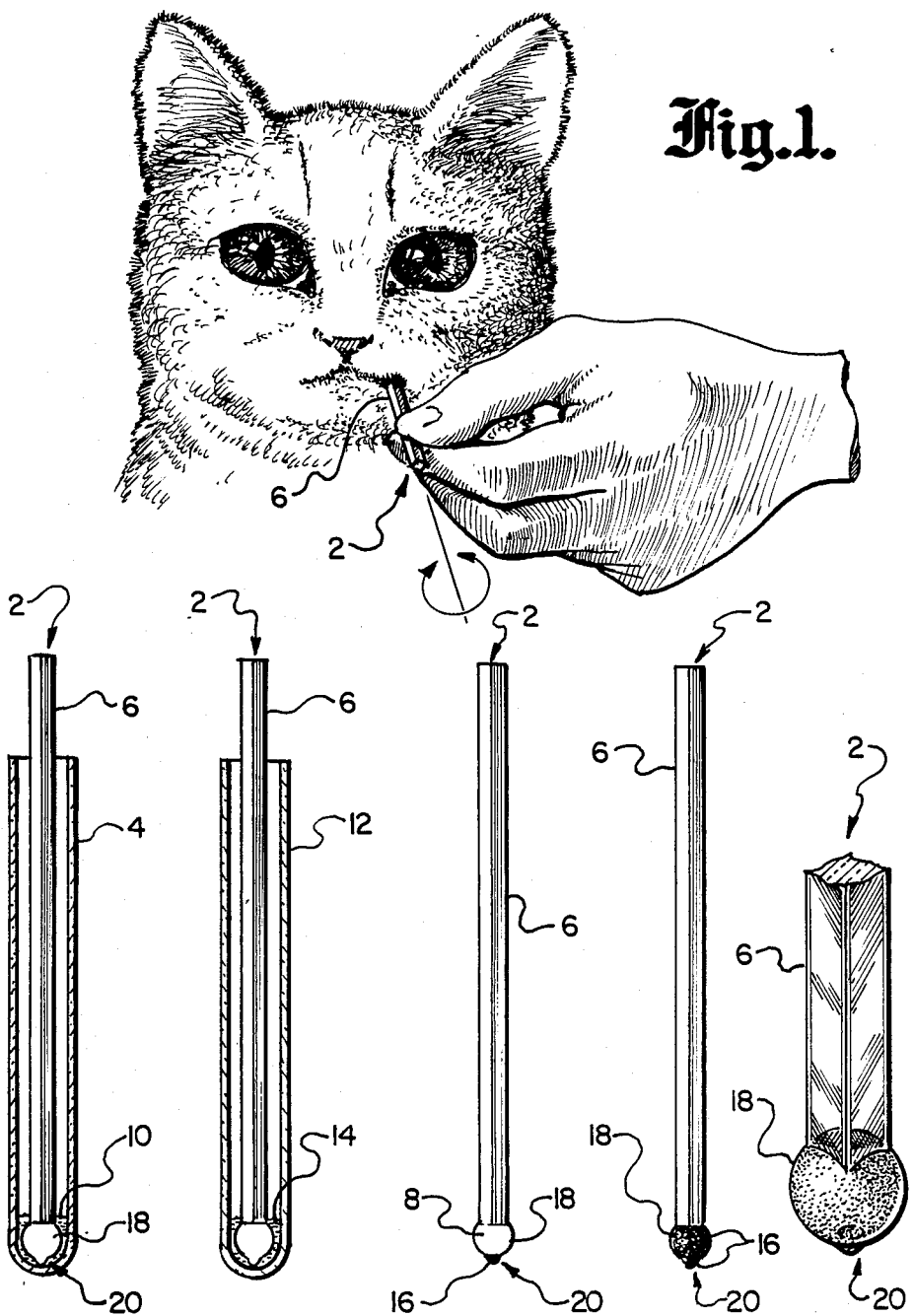
FIG. 1 is a perspective view of a FeLV test probe inserted into a cat's oral cavity towards the buccal crease illustrating the process of rotating the probe.
FIG. 2 is a perspective view of the probe of FIG. 1 inserted into an incubation vessel illustrating the submersion of the immunochemically sensitive member of the probe within an incubation reagent. The nipple shaped control submember is shown to support the test submember slightly above the bottom of the incubation vessel, the shape of which minimizes the volume of incubation reagent required to surround the test submember.
FIG. 3 is a perspective view of the probe of FIG. 2 inserted into a development vessel and submerged in a chromogenic substrate.
FIG. 4 is a perspective view of the probe of FIG. 3 illustrating a negative color development on the test submember, indicating an absence of FeLV and/or FeLV antigens in the saliva sample, and a positive color development on the control submember, indicating that the incubation and development reagents are active.
FIG. 5 is a perspective view of the probe of FIG. 3 illustrating a positive color development on the test submember, indicating the presence of FeLV and/or FeLV antigens in the saliva sample, and a positive color development on the control submember.
FIG. 6 is an enlarged fragment of the probe of FIG. 5 illustrating the frosted texture of the immunochemically sensitive member with positive color development.

The FeLV saliva test employs an immunological probe (2) for acquiring the saliva sample, for transferring the saliva sample to the incubation vessel (4), and for developing the color reactions which indicate the presence or absence of the FeLV and FeLV antigens. The immunological probe (2) includes a handle (6) and an immunochemically sensitive member (8) coated with anti-FeLV antibody. Prior to use, the immunochemically sensitive member (8) should be washed under water. Using the handle (6), the user then inserts the washed immunochemically sensitive member (8) into the cat's buccal crease, i.e. the posterior portion of the cat's oral cavity between the jaw and the buccal surface. The cat tend to avoid efforts to depress their tongue. The probe (2) may then be axially rotated within the buccal crease so as to uniformly wet the immunochemically sensitive member (8) with a sample of the cat's saliva. The probe (2) is then removed from the cat's oral cavity. A sample of the cat's saliva will remain wetted onto the immunochemically sensitive member (8). The probe (2) is then transferred to an incubation vessel (4).

The incubation vessel (4) includes an incubating solution (10) having a composition which includes a soluble enzyme conjugate of anti-FeLV, with sufficient volume to submerge the immunochemically sensitive member (8). Incubation within the incubation vessel (4) allows FeLV and FeLV antigens in the saliva to bind to the immunochemically sensitive member (8) and to become immobilized thereon. Additionally, during the incubation, the soluble enzyme conjugate (10) will bind both to soluble FeLV and FeLV antigens within the saliva and to immobilized FeLV and FeLV antigens attached to the immunochemically sensitive member (8). Binding of enzyme conjugate (10) to the immobilized FeLV and FeLV antigens causes the immunochemically sensitive member (8) to become enzymically labelled. After the incubation step, the probe (2) is then removed from the incubation vessel (4) and rinsed so as to remove unbound enzyme conjugate from contact with the immunochemically sensitive member (8), leaving behind only specifically bound enzyme conjugate attached to the immunochemically sensitive member (8).

After being rinsed, the probe (2) is then developed by means of a chromogenic substrate. The probe (2) is inserted into a developing vessel (12) containing a developing solution (14) having a composition which includes the chromogenic substrate. If enzyme conjugate remains bound to the probe (2) after the rinsing step, exposure to the chromogenic substrate (14) will cause the development of color (16). The development of color (16) indicates the presence of FeLV and FeLV antigens in the saliva sample.

A preferred embodiment of the probe (2) is shown in FIG.'S 4 & 5. The probe (2) resembles the appearance of a swizzle stick. The probe (2) has a plastic composition, perferably of polystyrene. The probe (2) includes a long handle (6) and an immunochemically sensitive member (8). The handle (6) is approximately 3–4 inches long and 1/8–3/16 inch in diameter. The length is sufficient to enable a veterinary clinician to insert the probe (2) to the posterior oral cavity between the cat's jaw and the buccal surface. The immunochemically sensitive member (8) of the probe (2) includes a test submember (18) which attaches to the handle (6) and an optional control submember (20). In the preferred embodiment the test submember (18) has a ball like shape and the control submember (20) has a nipple like shape which attaches to the test submember (18) and extending from the test submember (18) in a direction opposite the handle (6). The ball shaped test submember (18) has a diameter of approximately 3/16–5/16 inch. The ball like shape of the test submember (18) serve to blunt the impact and contact between the immunochemically sensitive member (8) and the cat's oral cavity when it is inserted by the veterinary clinician. The ball like shape of the test submember (18) also serves to indicate to the user which end is immunochemically sensitive.

The shape of the test submember (18) is adapted to conform to the shape of the incubation vessel (4). FIG. 2 illustrates that the diameter of the test submember (18) is only slightly smaller than the bore of the incubation vessel (4). The close fit between the test submember (18) and the incubation vessel (4) allows a small volume of liquid to submerge the test submember (18) when the probe (2) is introduced into the incubation vessel (4). FIG. 2 also illustrates a nipple shaped control submember (20) extending from the test submember (18). The control submember (20) rests on the bottom of the incubation vessel (4) and serves to support and raise the test submember (18) off the bottom of the incubation vessel (4). In this manner, the liquid within the incubation vessel (4) is more uniformly distributed around the test submember (18) and minimizes the diffusion distances and the duration of the incubation period.

The surface of the test submember (18) is etched or frosted. If the probe (2) is composed of polystyrene, this etching or frosting may be accomplished during the molding process. The frosted surface serves two functions. Firstly, the frosted surface has an improved wettability, i.e. when contacted with saliva, the saliva will tend to adhere to the frosted surface. Secondly, the frosted surface has a comparatively increased surface area which increases the amount of anti-FeLV antibody which can be coated onto it.

The immunochemically sensitive member (8) is rendered immunochemically sensitive by coating its respective submembers with various types of antibody. The test submember (18) is coated with anti-FeLV antibody by passive adsorption. The control submember (20) is coated with anti-mouse IgG antibody. To fabricate the embodiment illustrated in FIG. 4, the control submember (20) should be coated first. The control submember (20) may be coated by incubating the nipple shaped portion for three or four hours at room temperature (25° C.) in a solution of anti-mouse IgG (2–5 micrograms immunoglobulin/ml) in pH 9.2 sodium borate buffer. The volume of anti-mouse IgG solution should be sufficiently small so that it covers only the nipple shaped portion of the control submember (20), i.e. without significant contact between the anti-mouse IgG and the ball shaped test submember (18). After the control submember (20) is coated, the test submember (18) may then be coated. The test submember (18) is then incubated, together with the control submember (20) for three or four hours at room temperature (25° C.) in a solution of anti-FeLV antibody (2-5 micrograms immunoglobulin/ml) in pH 9.2 sodium borate buffer. The anti-FeLV antibody may be either polyclonal or monoclonal. If monoclonal anti-FeLV antibody is employed, it may have a specificity for p27, the nucleocapsid protein of FeLV. The volume of anti-FeLV immunoglobulin solution should be sufficient to submerge the entire test submember (18). After the test submember (18) is coated with anti-FeLV antibody, it may then be treated with BSA by incubating for three hours in 1% BSA, pH 7.4 PBS. After this third incubation, the device is then washed in 0.05% Tween-20, PBS, and allowed to air dry at room temperature (25° C.) for 24 hours. Treatment with BSA reduces nonspecific binding to the antibody coated portions of the device during subsequent immunoassays. For maximum stability, the probes are then stored dry at 4° C.

The test submember (18) may have a variety of shapes. FIG. 1 illustrates an embodiment having a spherical shape. However, a variety of elipsoidal, oblong, oblate, egg shaped, and other shapes may be employed. The shape of the test submember (18) is restricted by the following requirements: the shape should be acceptable to the cat for insertion into its buccal crease; the shape should conform to the interior configuration of the bottom of the incubation vessel (4), so as to help minimize the incubation period; the shape should help to blunt the contact between the immunochemically sensitive member (8) and the oral cavity; the shape should help to provide a uniformly wettable surface for acquiring the saliva sample when rotated within the buccal crease; and the shape should help the user to distinguish between the immunochemically sensitive member (8) and the handle (6).

After the incubation step, the probe (2) is then rinsed of free unattached enzyme conjugate and submitted to a development step. During the development step the immunochemically sensitive member (8) is treated with a chromogenic substrate (14). The composition of the chromogenic substrate (14) will depend upon the particular enzyme employed in the enzyme conjugate. The composition of the chromogenic substrate (14) will also depend whether precipitable or nonprecipitable color products are desired. The use of precipitating chromogenic substrates causes chromophores to precipitate directly onto the immunochemically sensitive member (8), thereby causing the immunochemically sensitive member (8) to change its color (16). If a control submember (20) is employed with the device, the development of color (16) on the control submember (20) indicates that both the enzyme conjugate (10) and the chromogenic substrate (14) are active. On the other hand, the use of non-precipitating chromogenic substrates (14) causes a color (16) change observable in the development reagent itself. Non-precipitating chromogenic substrates can not be used with probes having an integrally attached control submember (20). Inclusion of such a control submember (20) would always cause the development reagent to change color, whether FeLV was present or not. If a control is desired when using a nonprecipitating chromogenic substrate, the control must consist of a separate probe coated with anti-IgG antibody and incubated separately and in parallel with the enzyme conjugate.

EXAMPLE 1

FeLV Saliva Test Employing Alkaline Phosphatase and A Precipitating Chromogenic Substrate FeLV tests which employ precipitating chromogenic substrates (14) may include a control submember (20) integrally attached to the test submember (18). The nipple shaped control submember (20) and the ball shaped test submember (18) should be coated with anti-mouse IgG antibody and anti-p27 monoclonal antibody respectively, as described above. After collecting the saliva sample, the immunochemically sensitive member (8) is then incubated in an incubation vessel (4) containing a soluble enzyme conjugate of anti-FeLV (10).

Soluble enzyme conjugate (10) is prepared from alkaline phosphatase and anti-p27 monoclonal antibody, according to the method of Nakane, et al. (Nakane, P. K., and Kawaio, A. T., Histochem and Cytochem, Vol. 22, 1084 (1974)). The alkaline phosphatase covalently coupled to the anti-p27 monoclonal antibody, i.e. the nucleocapsid protein of FeLV, to form the enzyme conjugate.

After incubating the immunochemically sensitive member (8) with the enzyme conjugate (10) for approximately 15 minutes, the immunochemically sensitive member (8) is then rinsed under cold tap water to remove unbound enzyme conjugate. The enzyme conjugate which remains bound to immobilized FeLV and FeLV antigens allows the immunochemically sensitive member (8) to be color developed. The immunochemically sensitive member (8) is then developed in a chromogenic substrate (14) solution containing 3.4 mg/ml indoxyl phosphate in a buffer of 0.1 M diethanolamine at pH 9. The alkaline phosphatase converts the indoxyl phosphate into a product which dimerizes and precipitates onto the immunochemically sensitive member (8), depositing a distinctive indigo color. The deposit of an indigo color on the control submember (20) indicates that the alkaline phosphatase and the indoxyl phosphate are active. The deposit of an indigo color on the test submember (18) indicates that FeLV and FeLV antigens were present in the saliva sample.

EXAMPLE 2

FeLV Saliva Test Employing Horseradish Peroxidase and Non-Precipitating Chromogenic Substrate The test is the same as in Example 1 except that no control submember (20) is attached to the probe (2); except that horseradish peroxidase is substituted for alkaline phosphatase; and except that a different chromogenic substrate (14) is employed. The chromogenic substrate (14) is composed of a phosphate buffered saline (PBS) containing 0.5 mg/ml of 3,3',5,5'-tetramethylbenzidine (TMB) and 1.5 mM hydrogen peroxide, or 1.5 mM urea peroxide. When developed with this chromogenic substrate, a blue diimine color develops in the substrate solution. It does not despoist onto the immunochemically sensitive member (8). If a control is desired, a second control probe coated with anti-mouse IgG antibody must be employed and separately incubated and developed.

What is claimed is:

1. A probe for acquiring a saliva sample from the oral cavity of a cat, comprising:

an immunochemically sensitive member having a test submember coated with immobilized anti-p27 antibody for binding and immobilizing p27 antigens and feline leukemia virus particles from said saliva sample, the test submember having a surface wettable by cat saliva, and a handle connected to said immunochemically sensitive member, said handle being sized to allow insertion of said immunochemically sensitive member into the oral cavity of a cat and manipulation of said immunochemically sensitive member within said oral cavity for acquiring said saliva sample.

2. The probe as described in claim 1, wherein said immunochemically sensitive member has a frosted surface.

3. The probe as described in claim 1, wherein said immunochemically sensitive member has a spherical shape.

4. The probe as described in claim 1, wherein said immunochemically sensitive member further comprises a control submember coated with anti-immunoglobulin antibody having a specificity for binding an anti-p27 antibody component of a soluble enzyme conjugate of anti-p27.

5. The probe as described in claim 4, wherein said control submember has a nipple shape extending from the test submember in a direction opposite said handle.

6. The probe as described in claim 5, wherein said immunochemically sensitive member has a frosted surface.

7. A method for detecting a feline leukemia virus (FeLV) infection in a cat, comprising:

inserting a probe into a cat's oral cavity, the probe comprising an immunochemically sensitive member having a test submember coated with immobilized anti-p27 antibody and having a wettable surface, then contacting said immunochemically sensitive member with saliva in the cat's oral cavity, thereby wetting a sample of the cat's saliva onto said member, then removing said probe from the cat's oral cavity, then transferring said probe to an incubation vessel, said vessel containing an incubation solution comprising a soluble enzyme conjugate of anti-p27 antibody, the volume of the incubation solution being sufficient for submerging said immunochemically sensitive member, then incubating said immunochemically sensitive member with said incubation solution under conditions suitable for binding p27 antigens and FeLV particles in the saliva sample to both the immobilized anti-p27 antibody and the soluble enzyme conjugate, whereby p27 antigens or FeLV particles become sandwiched between said immobilized anti-p27 antibody and said soluble anti-p27 antibody of the enzyme conjugate, the enzyme conjugate thereby becoming bound onto the test submember in proportion to the presence of p27 antigens and FeLV particles in the saliva sample, then removing said probe from said incubation vessel, then rinsing unbound soluble enzyme conjugate of anti-p27 antibody from said probe, then developing the bound enzyme conjugate of anti-p27 antibody remaining on said probe by contacting and incubating the washed probe with a developing solution containing a chromogenic substrate for said enzyme, and then observing the development of a color specific for the presence of the bound enzyme conjugate.

8. The method of claim 7, further comprising the step of washing the probe prior to said insertion step.

9. The method of claim 7, wherein in said contacting step, the saliva is wetted onto said immunochemically sensitive member by simultaneously axially rotating the probe within the saliva while contacting said saliva.

10. The method of claim 7, wherein in said insertion and contacting steps, said immunochemically sensitive member is placed in the posterior position of the cat's oral cavity between the jaw and the buccal surface.

11. The method of claim 7, wherein the immunochemically sensitive member of the probe further comprises a control submember coated with an anti-immunoglobulin antibody bindable to the anti-p27 antibody component of the soluble enzyme conjugate, and, subsequent to said developing step, said method comprises checking the development of color on the control submember.

12. The method of claim 7, wherein in said development step, the solution of chromogenic substrate includes a precipitating substrate.

13. The method of claim 12, wherein the enzyme component of said soluble enzyme conjugate of anti-p27 antibody is alkaline phosphatase and the solution of chromogenic substrate includes indoxyl phosphate.

14. The method of claim 7, wherein in said developing step, the solution of chromogenic substrate includes a non-precipitating substrate.

15. The method of claim 14, wherein the enzyme component of said soluble enzyme conjugate of anti-p27 is horseradish peroxidase and the solution of chromogenic substrate includes 3,3',5,5'-tetramethylbenzidine and a source of hydrogen peroxide.

16. A kit for acquiring a saliva sample from the oral cavity of a cat and for detecting feline leukemia virus (FeLV) infection in said cat, comprising:

a probe for acquiring the saliva sample, said probe comprising a handle and an immunochemically sensitive member having a test member coated with immobilized anti-p27 antibody, said handle being connected to the immunochemically sensitive member to allow insertion of said member into the oral cavity of a cat and manipulation of said member for acquiring a saliva sample, an incubation solution including a soluble enzyme conjugate of an anti-p27 antibody, an incubation vessel shaped to contain said incubation solution and to closely fit around said immunochemically sensitive member of said probe, a developing solution containing a chromogenic substrate capable of generating color in the presence of said soluble enzyme conjugate, and a container sized to contain said probe, said incubation solution, said developing solution, and said incubation vessel.

17. A kit as described in claim 16, wherein said immunochemically sensitive member includes a control submember coated with an anti-immunoglobulin antibody bindable to said anti-p27 antibody component of the soluble enzyme conjugate.

18. The kit as described in claim 16, wherein said immunochemically sensitive member includes a nipple extending in a direction opposite said handle, wherein when said immunochemically sensitive member is located in said incubation vessel, said nipple supports said member to provide a substantially uniform distribution of said incubation solution around said member.

19. The kit as described in claim 16, wherein said immunochemically sensitive member has a ball shape complementary to the shape of said incubation vessel for minimizing the required volume of said incubation solution.

* * * * *